US011170897B2

(12) United States Patent
Stumpe et al.

(10) Patent No.: US 11,170,897 B2
(45) Date of Patent: Nov. 9, 2021

(54) METHOD AND SYSTEM FOR ASSISTING PATHOLOGIST IDENTIFICATION OF TUMOR CELLS IN MAGNIFIED TISSUE IMAGES

(71) Applicant: Google LLC, Mountain View, CA (US)

(72) Inventors: Martin Christian Stumpe, Belmont, CA (US); Lily Peng, Mountain View, CA (US); Yun Liu, Mountain View, CA (US); Krishna K. Gadepalli, Mountain View, CA (US); Timo Kohlberger, Mountain View, CA (US)

(73) Assignee: Google LLC, Mountain View, CA (US)

( * ) Notice: Subject to any disclaimer, the term of this patent is extended or adjusted under 35 U.S.C. 154(b) by 123 days.

(21) Appl. No.: 16/488,029

(22) PCT Filed: Feb. 23, 2017

(86) PCT No.: PCT/US2017/019051
§ 371 (c)(1),
(2) Date: Aug. 22, 2019

(87) PCT Pub. No.: WO2018/156133
PCT Pub. Date: Aug. 30, 2018

(65) Prior Publication Data
US 2020/0066407 A1    Feb. 27, 2020

(51) Int. Cl.
*G16H 50/20*       (2018.01)
*G06T 7/11*        (2017.01)
(Continued)

(52) U.S. Cl.
CPC .......... *G16H 50/20* (2018.01); *G01N 33/4833* (2013.01); *G06K 9/6256* (2013.01);
(Continued)

(58) Field of Classification Search
CPC .......... G16H 30/40; G16H 50/20; G06T 7/11; G06T 7/0012; G06T 2207/10056;
(Continued)

(56) References Cited

U.S. PATENT DOCUMENTS 10,460,211 B2    10/2019   Vanhoucke et al.
2006/0018524 A1*   1/2006   Suzuki ................. G06K 9/6292
                                                         382/128
(Continued)

OTHER PUBLICATIONS

Frazão X., Alexandre L.A. (2014) Weighted Convolutional Neural Network Ensemble. In: Bayro-Corrochano E., Hancock E. (eds) Progress in Pattern Recognition, Image Analysis, Computer Vision, and Applications. CIARP 2014. Lecture Notes in Computer Science, vol. 8827. Springer, Cham. (Year: 2014).*
(Continued)

*Primary Examiner* — Kenny A Cese
(74) *Attorney, Agent, or Firm* — McDonnell Boehnen Hulbert & Berghoff LLP

(57) ABSTRACT

A method, system and machine for assisting a pathologist in identifying the presence of tumor cells in lymph node tissue is disclosed. The digital image of lymph node tissue at a first magnification (e.g., 40×) is subdivided into a multitude of rectangular "patches." A likelihood of malignancy score is then determined for each of the patches. The score is obtained by analyzing pixel data from the patch (e.g., pixel data centered on and including the patch) using a computer system programmed as an ensemble of deep neural network pattern recognizers, each operating on different magnification levels of the patch. A representation or "heatmap" of the slide is generated. Each of the patches is assigned a color or grayscale value in accordance with (1) the likelihood of malignancy score assigned to the patch by the combined outputs of the ensemble of deep neural network pattern recognizers and (2) a code which assigns distinct colors (or
(Continued)

grayscale values) to different values of likelihood of malignancy scores assigned to the patches.

20 Claims, 7 Drawing Sheets

(51) Int. Cl.
| | |
|---|---|
| G16H 30/40 | (2018.01) |
| G06K 9/62 | (2006.01) |
| G06T 7/00 | (2017.01) |
| G06T 11/00 | (2006.01) |
| G01N 33/483 | (2006.01) |

(52) U.S. Cl.
CPC .............. *G06T 7/0012* (2013.01); *G06T 7/11* (2017.01); *G06T 11/001* (2013.01); *G16H 30/40* (2018.01); *G06K 2209/05* (2013.01); *G06T 2207/10056* (2013.01); *G06T 2207/20081* (2013.01); *G06T 2207/30024* (2013.01); *G06T 2207/30168* (2013.01)

(58) Field of Classification Search
CPC . G06T 2207/20081; G06T 2207/30024; G06T 2207/30168; G06T 2207/20084; G06T 11/001; G01N 33/4833; G06K 9/6256; G06K 9/00147; G06N 3/0454; G06N 3/08; G06F 15/76
See application file for complete search history.

(56) References Cited

U.S. PATENT DOCUMENTS

| | | | | |
|---|---|---|---|---|
| 2008/0044080 | A1* | 2/2008 | Li | G06K 9/4609 382/155 |
| 2012/0136255 | A1 | 5/2012 | Fan et al. | |
| 2013/0156279 | A1 | 6/2013 | Schoenmeyer et al. | |
| 2015/0063667 | A1* | 3/2015 | Sprencz | A61B 6/505 382/131 |
| 2016/0063359 | A1 | 3/2016 | Szegedy et al. | |
| 2016/0328606 | A1* | 11/2016 | Bourdev | G06K 9/00362 |
| 2017/0032244 | A1* | 2/2017 | Kurata | G06N 3/0472 |

OTHER PUBLICATIONS

F. A. Spanhol, L. S. Oliveira, C. Petitjean and L. Heutte, "Breast cancer histopathological image classification using Convolutional Neural Networks," 2016 International Joint Conference on Neural Networks (IJCNN), Vancouver, BC, Canada, 2016, pp. 2560-2567, doi: 10.1109/IJCNN.2016.7727519. (Year: 2016).*
Le Hou, Dimitris Samaras, Tahsin M. Kurc, Yi Gao, James E. Davis, Joel H. Saltz; Patch-Based Convolutional Neural Network for Whole Slide Tissue Image Classification. Proceedings of the IEEE Conference on Computer Vision and Pattern Recognition (CVPR), 2016, pp. 2424-2433 (Year: 2016).*
Wang, D., Khosla, A., Gargeya, R., Irshad, H., & Beck, A. (2016). Deep Learning for Identifying Metastatic Breast Cancer. ArXiv, abs/1606.05718. (Year: 2016).*
N. Bayramoglu, J. Kannala and J. Heikkilä, "Deep learning for magnification independent breast cancer histopathology image classification," 2016 23rd International Conference on Pattern Recognition (ICPR), Cancun, Mexico, 2016, pp. 2440-2445, doi: 10.1109/ICPR.2016.7900002. (Year: 2016).*
D. Mahapatra, P. K. Roy, S. Sedai and R. Garnavi, "A CNN based neurobiology inspired approach for retinal image quality assessment," 2016 38th Annual International Conference of the IEEE Engineering in Medicine and Biology Society (EMBC), Orlando, FL, USA, 2016, pp. 1304-1307, (Year: 2016).*
V. Gupta and A. Bhavsar, "Breast Cancer Histopathological Image Classification: Is Magnification Important?," 2017 IEEE Conference on Computer Vision and Pattern Recognition Workshops (CVPRW), Honolulu, HI, 2017, pp. 769-776, doi: 10.1109/CVPRW.2017.107. (Year: 2017).*
"Breast cancer histopathological image classification using Convolutional Neural Networks", Fabio Alexandre Spanhol et al., 2016 International Joint Conference On Neural Networks (IJCNN), IEEE, pp. 2560-2567 (Jul. 24, 2016).
"Mitosis Detection in Breast Cancer Histology Images with Deep Neural Networks", Dan C. Ciresan et al., Annual International Conference on the Theory and Applications of Cryptographic Techniques, Eurocrypt 2018, Springer, Berlin, Heidelberg, pp. 411-418 (Sep. 22, 2013).
"Locality Sensitive Deep Learning for Detection and Classification of Nuclei in Routine Colon Cancer Histology Images", Sirinukunwattana Korsuk et al., IEEE Transactions on Medical Imaging, vol. 35, No. 5 , pp. 1196-1206 (May 1, 2016).
"Pathology imaging informatics for quantitative analysis of whole-slide images", Kothari Sonal et al., Journal of the American Medical Informatics Association, vol. 20, No. 6, pp. 1099-1108 (Nov. 1, 2013).
"Histopathological Image Analysis: A Review", M. N. Gurcan et al., IEEE Reviews in Biomedical Engineering, IEEE, USA, vol. 2, pp. 147-171 (Jan. 1, 2009).
PCT International Search Report and Written Opinion, PCT International Application No. PCT/US2017/019051, dated May 4, 2017, 11 pages.
"Deep Learning as a Tool for Increasing Accuracy and Efficiency of Histopathological Diagnosis"; Geert Litjens, et al.; Scientific Reports | 6:26286 | DOI: 10.1038/srep26286 (May 23, 2016).
"Deep Learning for Identifying Metastatic Breast Cancer"; Dayong Wang, et al.; arXiv:1606.05718v1 (Jun. 18, 2016).
"Image Analysis and Machine Learning in Digital Pathology: Challenges and Opportunities"; Anant Madabhushi, et al.; Medical Image Analysis 33, pp. 170-175 (Jul. 4, 2016).
"H&E-stained Whole Slide Deep Learning Predicts SPOP Mutation State in Prostate Cancer"; Andrew J. Schaumbert, et al.; bioRxiv preprint; http://biorxiv.org/content/early/2016/07/17/064279 (Jul. 17, 2016).
"Softmax Regression"; Unsupervised Feature Learning and Deep Learning Tutorial; retrieved from URL: http://ufldl.stanford.edu/tutorial/supervised/SoftmaxRegression/; formatted version, as well as version retrieved from archive.org corresponding to (Dec. 5, 2016) included.
"Going Deeper with Convolutions"; Christian Szegedy, et al.; arXiv:1409.4842v1 (Sep. 17, 2014).
"Rethinking the Inception Architecture for Computer Vision"; Christian Szegedy, et al.; arXiv:1512.00567v3 (Dec. 11, 2015).
"Inception-v4, Inception-ResNet and the Impact of Residual Connections on Learning"; Christian Szegedy, et al.; arXiv:1602.07261v2 (Aug. 23, 2016).
"Evaluating Stability of Histomorphometric Features Across Scanner and Staining Variations: Prostate Cancer Diagnosis from Whole Slide Images"; Patrick Leo, et al.; Journal of Medical Imaging 3(4), 047502 (Dec. 2016).
"Stain Specific Standardization of Whole Slide Histopathological Images"; Babak Ehteshami Bejnordi, et al.; IEEE Transactions on Medical Imaging; DOI 11.1109/TMI.2015.2476509 (Feb. 2016).
"Hue-Saturation-Density (HSD) Model for Stain Recognition in Digital Images from Transmitted Light Microscopy" Jeroen A.W.M. van der Laak, et al.; Cytometry 39:275-284 (2000).
"The Linear Monge-Kantorovitch Linear Colour Mapping for Example-Based Colour Transfer"; F. Pitie', et al.; 4th European Conference on Visual Media Production (2007).

* cited by examiner

Original Slide Image

Ground Truth Mask white: tumor
black: no tumor

Tumor Probability heatmap red: high tumor probability
blue: low tumor probability
black: no tissue

METHOD AND SYSTEM FOR ASSISTING PATHOLOGIST IDENTIFICATION OF TUMOR CELLS IN MAGNIFIED TISSUE IMAGES

CROSS-REFERENCE TO RELATED APPLICATION

The present application is a national stage entry of PCT/US2017/019051 filed Feb. 23, 2017, the content of which is hereby incorporated by reference.

FIELD

This disclosure relates generally to the field of digital pathology and more particularly to methods and systems for assisting a pathologist in identifying the presence of tumor cells (i.e., cancer) in a magnified digital image of tissue, such as for example lymph node tissue, or breast or prostate cancer tissue obtained from a biopsy.

BACKGROUND

The assessment of lymph nodes for metastasis is central the staging of many types of solid tumors, including breast cancer. The process requires highly skilled pathologists and is fairly time-consuming and error-prone, especially for nodes that are negative for cancer or have a small foci of cancer. The current standard of care involves examination of digital slides of nodes biopsies that have been stained with hematoxylin and eosin (H&E) However, there are several limitations inherent with manual reads including reader fatigue, and intra and inter-grader reliability that negatively impact the sensitivity of the process. Accurate review and assessment of lymph node biopsy slides is important because the presence of tumor cells in the lymph node tissue may warrant new or more aggressive treatment for the cancer and improve the patient's chances of survival.

The prior art includes descriptions of the adaptation of deep learning techniques and trained neural networks to the context of digital tissue images in order to improve cancer diagnosis, characterization and/or staging. Pertinent background art includes the following articles: G. Litjens, et al., *Deep learning as a tool for increasing accuracy and efficiency of histopathological diagnosis* (May 2016); D. Wang et al., *Deep Learning for Identifying Metastatic Breast Cancer* (June 2016); A. Madabhushi et al., *Image analysis and machine learning in digital pathology: Challenges and opportunities*, Medical Image Analysis 33 p 170-175 (2016); A. Schuamberg, et al., *H&E-stained Whole Slide Deep Learning Predicts SPOP Mutation State in Prostate Cancer.*

SUMMARY

In one aspect, a method for analyzing a tissue biopsy is described. The method includes the steps of (a) receiving image data representing tissue from the tissue biopsy, the image data obtained at a first magnification; (b) subdividing the image data into a plurality of patches, each patch comprising a portion of the image data representing a respective portion of the tissue from the tissue biopsy; and (c) for each of the patches, determining a likelihood of malignancy score, wherein the score is obtained by processing the patch using an ensemble of deep neural network pattern recognizers and combining the outputs of each of the deep neural network pattern recognizers, wherein the ensemble of deep neural network pattern recognizers are arranged to process the patch at a plurality of levels of magnification including the first magnification and a second magnification.

In a further aspect, a method for assisting a pathologist in identifying the presence of tumor cells in magnified digital image of tissue obtained from a biopsy is disclosed. The tissue is fixed on a slide, stained (e.g., with H&E) and scanned by a digital slide scanner. The method involves obtaining a digital image at a first magnification (e.g. 40×) of the slide. The digital image is then subdivided into a multitude of "patches." Each patch is a two dimensional array of pixels (e.g., square or rectangle) from the digital image, e.g., 128×128 or 299×299 pixels. Thus, each patch is a portion of the image data representing a respective portion of the tissue from the tissue biopsy.

A likelihood of malignancy score is then determined for each of the patches. The score is obtained by analyzing pixel data in the digital image including the patch (e.g., pixel data centered on and including the patch) using an ensemble of deep neural network pattern recognizers. The pixel data including the patch is analyzed by the ensemble at multiple levels of magnification including the first magnification (e.g., 40×) and a second magnification centered on or containing the patch, e.g., 20×. In one embodiment, the pixel data is analyzed by the ensemble at four different magnifications, including 5×, 10×, 20× and 40×. The pixel data for the second magnification (and optionally additional magnifications) can be obtained from a second or additional scan(s) of the slide, or from a downsampling or upsampling of the original digital slide image data. Each member of the ensemble generates an output (e.g., score) and the outputs are combined to generate of overall output or score for the patch. Various methods for combining the outputs are described in detail below, including calculation of average, median, or weighted average, or combining the outputs with the use of a convolutional neural network.

A representation of the slide is generated for the user, e.g., displayed on a workstation display used by the pathologist. This representation is described in the following disclosure as a "heatmap". Basically, in the heatmap representation, each of the patches is assigned a color (or other alternative and equivalent representation, such as degree of grayscale) in accordance with (1) the likelihood of malignancy score assigned to the patch by the ensemble of deep neural network pattern recognizers and (2) a code, key or other assignment mechanism, which assigns distinct colors (or equivalently grayscale values) to different values of likelihood of malignancy scores assigned to the patches. For example, those areas (patches) with the highest scores indicating high likelihood of presence of tumor cells are shown as red areas and areas (patches) with lowest scores, low likelihood of presence of tumor cells, are blue or black. These heatmap representations are useful for directing the pathologist to particular areas of the slide to investigate for presence of tumor cells. In one embodiment, the heatmap representation is accompanied by a list of regions of interest, e.g., ranked by size.

In another aspect of the disclosure, a computer system programmed as a machine for assisting a pathologist in assessing the likelihood of presence of tumor cells in a magnified digital slide image containing tissue, such as lymph node or prostate tissue, is described. The computer system, which may take the form of a single programmed computer or a network of several computers, is in the form of an ensemble of deep neural network pattern recognizers, each of which are trained on a multitude of digital slide images of tissue at a particular and different magnification level, including slides of benign tissue and slides containing tumor cells. Each member of the ensemble generates an output in the form of a likelihood of malignancy score for a patch of a digital slide containing tissue (i.e., a slide of a particular patient being investigated by a pathologist). The outputs of each of the members of the ensemble are combined to generate an overall likelihood of malignancy score for the patch.

In still another aspect, a system is disclosed for assisting a user (e.g., pathologist) in identifying tumor cells in a tissue obtained from a biopsy. The system includes a workstation configured to display a magnified digital image of a slide containing the tissue. The system further includes an application programming interface (API) to a software system configured as an ensemble of deep neural network pattern recognizers, each trained on a training set comprising multitude of digital slide images of lymph node tissue at a particular and different magnification level of the digital slide images. The software system is further configured to subdivide the digital image into a multitude of patches, each patch in the form of a two dimensional array of pixels, such as rectangular or square. The software system is further configured for determining, for each of the patches, a likelihood of malignancy score, wherein the score is obtained by analyzing pixel data in the digital image including the patch using the ensemble of deep neural network pattern recognizers. The workstation is further configured to present on the display a representation of the slide wherein each of the patches is assigned a color or equivalent (e.g. grayscale value) in accordance with (1) the likelihood of malignancy score assigned to the patch by a combination of the outputs of the ensemble of deep neural network pattern recognizers and (2) a code, e.g., key or other assignment mechanism, which assigns distinct colors equivalently grayscale values) to different values of likelihood of malignancy scores assigned to the patches.

DETAILED DESCRIPTION

Overview and Methodology

In one aspect, this disclosure is directed to a method for assisting a pathologist in identifying the presence of tumor cells in magnified digital tissue images. The following discussion will be primarily in the context of identification of tumor cells in lymph node biopsies, however the architecture of the system, and the performance of the general method is the same for other types of tissue (e.g., detecting tumor cells in prostate or breast cancer tissue). The only difference is that the training slides for training the pattern recognizers of FIG. 5 may be selected from particular sets of tissue slides that are germane to the tissue of interest.

In any event, the tissue to be analyzed is fixed on a slide, stained and scanned by a digital slide scanner. Digital whole slide scanners and systems for staining slides are known in the art. Such devices and related systems are available from Aperio Technologies, Hamamatsu Photonics, Ventana Medical Systems, Inc., and others. The digital image can be obtained at a first magnification level (e.g. 40×), which is customary. The goal of assisting the pathologist is achieved by presenting to the pathologist on a display a "heatmap" image in which discrete areas (i.e., patches) of the slide which have a high probability of containing tumor cells are indicated in a particular color, e.g., dark red, whereas areas with relatively low probability of containing tumor cells are shown in a contrasting color, e.g., blue or violet. The heatmap image can be accompanied by a list of for example 10 different regions where there are groups of cells with a high probability of containing tumor cells. The pathologist is this directed or encouraged to review the areas highlighted in red or in the list of regions of interest and therefor there is an increased likelihood that areas containing tumor cells are not missed by the pathologist.

Figure 1A:
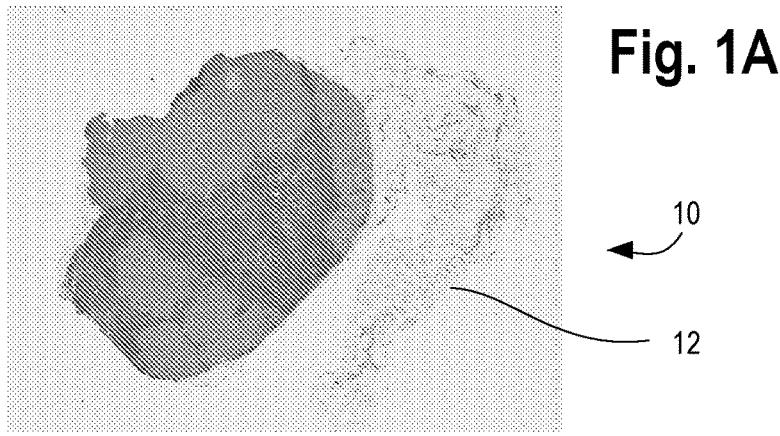
FIG. 1A illustrates a magnified digital image of a slide containing lymph node tissue stained with H&E.
Figure 1B:
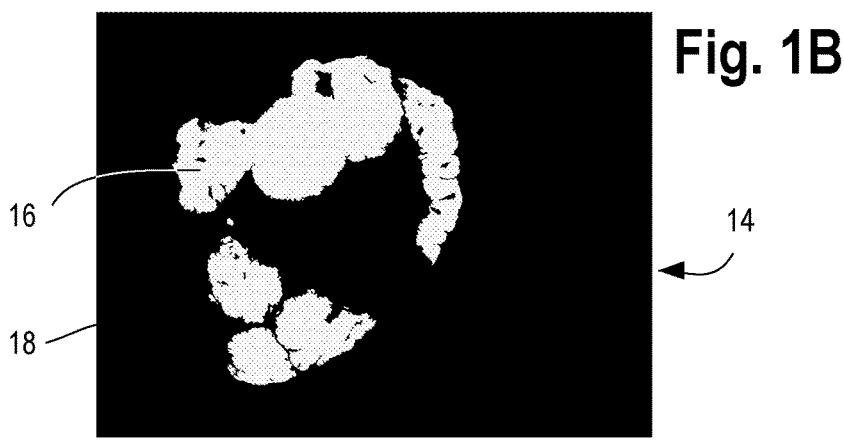
FIG. 1B is a ground truth image or mask of the slide image of FIG. 1A with the areas in white indicating areas where tumor cells are present and areas in black indicating areas where no tumor cells are present.
Figure 1C:
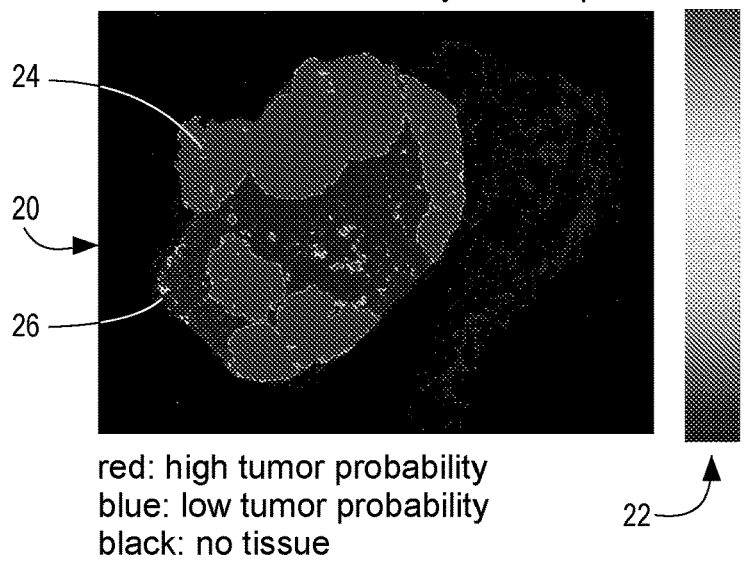
FIG. 1C is a heatmap image of the slide of FIG. 1A. The areas in red (indicated by reference number 24) are the areas where the corresponding patches have a high score indicating high probability of tumor cells, whereas the blue areas (indicated by reference number 26) are areas where the patches have a low score indicating low probability of tumor cells. Note that the areas in red in FIG. 1C correspond to the white (tumor) areas in FIG. 1B.

FIG. 1A illustrates a magnified digital image 10 of a slide containing lymph node tissue 12 stained with H&E. In such an image, it is not immediately obvious or apparent which regions of the image have a high likelihood of containing tumor cells. FIG. 1B is a ground truth image 14 or mask of the slide image of FIG. 1A with the areas in white 16 indicating areas where tumor cells are present and areas in black 18 indicating areas where no tumor cells are present, which is provided here for the sake of illustration but in practice may not be produced for a given slide of a patient biopsy. This ground truth image can be obtained from the use an immunohistochemical stain and analysis by a pathologist. FIG. 1C is a heatmap image 20 or representation of the slide of FIG. 1A, of the general kind that would be displayed on a workstation of a pathologist in accordance with this disclosure, see FIG. 7 below. The areas in red (indicated by reference number 24) are the areas where the corresponding patches have a high score indicating high probability of tumor cells, whereas the blue or violet areas (indicated by reference number 26) are areas where the patches have low scores indicating a low probability of containing tumor cells. Note that the white region 16 of FIG. 1B corresponds essentially to the area in red (24) of FIG. 1C, indicating that the red area 24 of the heatmap 20 of FIG. 1C correctly identifies the areas containing tumor cells. Similarly, the blue or violet area 26 of FIG. 1C corresponds to the black area 18 of FIG. 1B, indicating that the areas where the patches have low scores in fact do not contain tumor cells.

FIG. 1C also shows a code or key 22 which relates colors (or equivalently grayscale values) to scores which are assigned to patches in the image. The code or key 22 is shown in more detail in FIG. 2. The scores for each patch in the digital slide image range from 0.0 to 1.0. The areas of the heatmap 20 with the highest scores are shown as dark red, whereas the areas with the areas with the lowest scores are shown as violet. The code of FIG. 2 essentially uses the visible spectrum (i.e., colors of the rainbow) to assign colors to tumor probability scores. However, it would be possible to use only a portion of the visible spectrum. Moreover, in a less preferred alternative embodiment only degrees of grayscale could be used for the code, e.g., with white corresponding to a score of 0, black corresponding to score of 1, and degrees of gray making up the values between 0 and 1.

The methodology of generating the heatmap 20 of FIG. 1C will now be explained in conjunction with FIG. 3. At step 100, a biopsy of tissue potentially containing cancer cells (e.g., lymph node tissue) is obtained from a patient and is formalin fixed and paraffin embedded, optionally in a tissue block which is conventional. At step 102, the tissue block is sectioned, stained with H&E and laid on a clear glass slide. At step 104, the slide is digitally scanned by a whole slide digital slide scanner. At step 106, this scan produces a digitized image of the slide, scanned at 40×. The slide image is subdivided into a multitude of rectangular patches, such as ~12,000 or so. The number of patches per slide can range from 10,000 to 400,000. In one embodiment each patch is in the form of a square of 128×128 pixels or 299×299 pixels. The patches need not be square, and other two-dimensional configurations such as rectangles could be used. FIG. 4 shows a scanned lymph node tissue image 10 and a multitude of the patches 200, one of which is shown isolated in FIG. 4 showing the cellular details at 40×. The patches are not shown to scale.

The digital image is then accessed by or submitted to a computer and software system at 108. By way of overview, the system 108 is a machine-learning based software device that assists pathologists in the assessment for the presence of tumor cells in tissue specimens that have been formalin-fixed paraffin-embedded, stained with Hematoxylin and Eosin (H&E). Basically, in one embodiment the system includes three software components, including a first component 110 that provides image quality assessment for each of the patches, a second component 112 which calculates a likelihood of malignancy score between 0 and 1 on a per-patch basis, and a third component 114 which combines all the patches into a representation or heatmap (20, see FIG. 1C) for display to the pathologist on their workstation or device, including a ranked list of potential regions of interest based upon the size of the metastasis.

Image Quality Assessment 110

This component of the system 108 analyzes each patch to determine whether the image is of sufficient quality that it can be graded. This component 110 returns one of the following as an indicator of image quality for each patch of the image: Gradable, meaning that the patch is of a quality which is adequate for analysis by the software component 112, or Not Gradable, meaning that patch does not have an image quality which is adequate for analysis by software component 112. If Not Gradable is returned, the user could be instructed to either rescan the entire slide, or send the image patch for evaluation by a qualified pathologist. Not Gradable patches will be color coded gray in the heatmap in an embodiment with color for the code or key of FIG. 2.

It is also possible to perform quality control manually, e.g., by having a human rater label non-gradable patches or regions/groups of patches with quality control issues.

The performance of the image quality assessment in software component 110 is preferably performed by a trained pattern recognition neural network or other classification model. To develop such as model, human raters (pathologists) determine which patches in a set of H&E stained biopsy training slides are gradable or not gradable, and the resulting class-label patches are used as a training set for a pattern recognition neural network or other classification model. It is further contemplated that such a classification model or trained neural network could be added to the ensemble of trained pattern recognizers of FIG. 5 in a multi-headed model that will predict the gradability of an image patch.

Optionally, the system of 108 includes an automatic quality control module which evaluates the whole slide image for gradability (e.g., the presence of ink or other dirt on the slide, or evaluates whether the whole slide is out of focus, etc.). Such a QC module could be similarly generated as a trained neural network or classification model from class-labeled training slides.

Likelihood of Tumor Cells Scoring Software Component 112

The software component 112 evaluates each patch of pixels and generates a likelihood of malignancy score (i.e., the likelihood of tumor cells present in the patch) from between 0 and 1 for each patch.

The core prediction algorithm used by the component 112 is developed using a deep convolutional neural network approach to discern high-level patterns and features from a training set of a large collection of training tissue images (in this case, lymph node tissue images). Further discussion of this development method is provided in the description of FIG. 5. In the preferred embodiment, each member of an ensemble of deep neural network pattern recognizers analyze pixel information of the patch, including some surrounding pixels, and generates a probability score of between 0 and 1. Each member operates on a patch of pixels but at different magnification levels. Preferably, there are four such members in the ensemble. For example, one operates on a 128×128 patch at 40× magnification. Another operates on a 128×128 patch but at 20× magnification (centered on or containing the 128×128 patch at 40×). A third one operates on a 128×128 patch but at 10× (again, centered on or containing the 128×128 patch at 40×). A fourth one operates on a 128×128 patch at 5× (again, centered on or containing the 128×128 patch at 40×). The outputs of the four pattern recognizers are then combined, in the manner described below in conjunction with the description of FIG. 5.

To obtain the input patches at different magnifications the original pixel data at 40× is downsized or resampled to the corresponding magnification. In the situation where the original input image is 20× we upsample the image to create a 40× image out of it, and downsample the 20× image to obtain the 10× and 5× images. It is also possible to obtain four different digital images of the slide, one at each of 5×, 10×, 20× and 40×, thereby avoiding the need to downsample or upsample the images.

The advantage to using an ensemble of deep neural network pattern recognizers at different magnifications centered on or containing a given patch of pixels at 40× is that there are structures or features in the tissue images that are not fully revealed or difficult to accurately find in a pattern recognizer that operates at any one given magnification level, e.g., 40×. The overall sensitivity and performance of the pattern recognizer in module 112 is enhanced by performing pattern recognition at at least two different powers of magnification, and as stated here preferably at at least four different powers. This enhancement is made so that the algorithm can recognize different morphological or cellular features at the different magnifications, so that the eventual prediction reflects a comprehensive picture or analysis of the tissue that takes detail, as well as context, into account. This advantage is particularly noticed when the size of the training set of slide images becomes sufficiently large. Furthermore, the use of pattern recognizers trained at different magnifications is important for other cancer types, e.g. in prostate cancer we know that the overall tissue morphology is very important, and not only the appearance of the cell nuclei.

Figure 2:
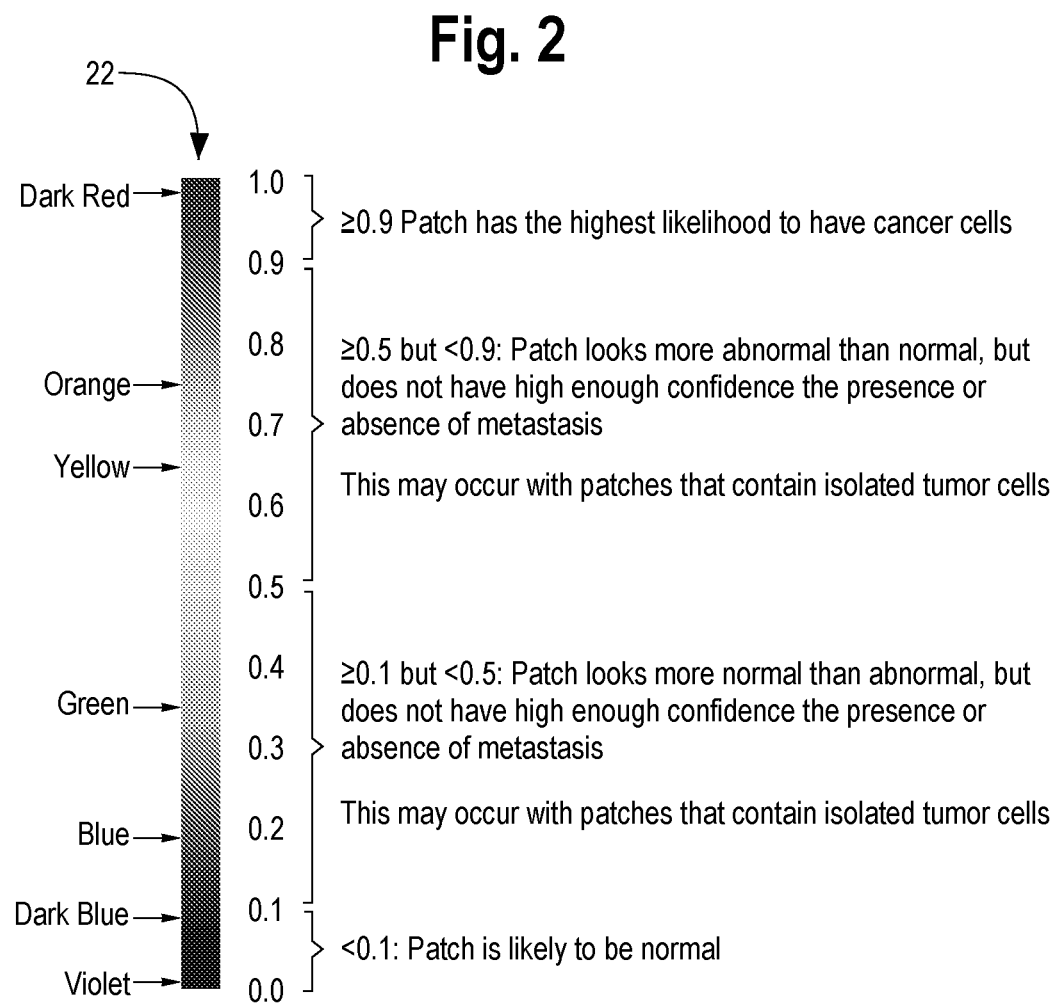
FIG. 2 is a detailed illustration of the code or key for assigning colors to patches based on tumor probability scores generated by the ensemble of deep neural network pattern recognizers. An analogous key would be used if grayscale instead of color is used for the heatmap.
Figure 3:
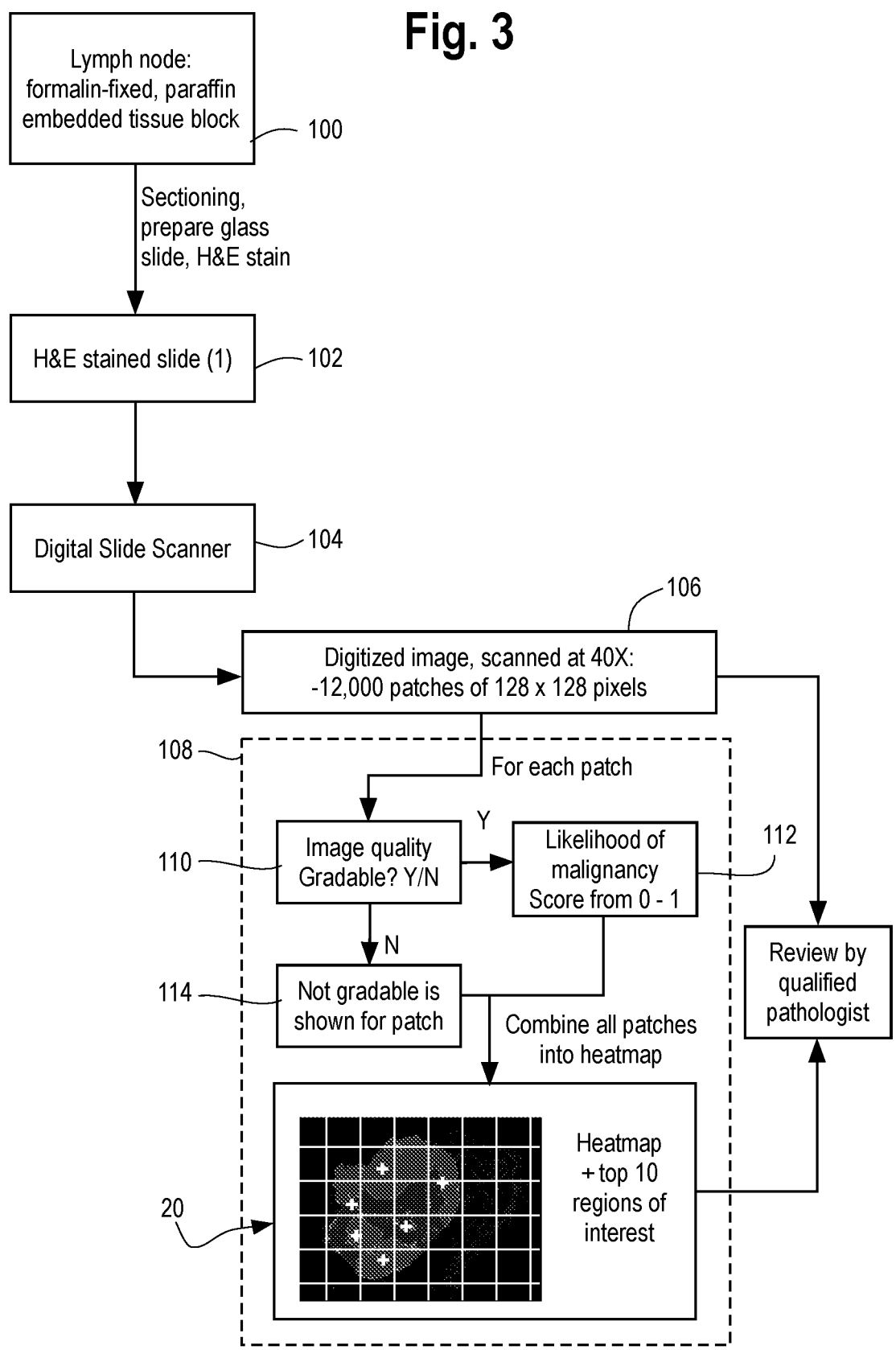
FIG. 3 is a flow chart showing a process and software architecture for generating the heatmap of FIG. 1C.
Figure 4:
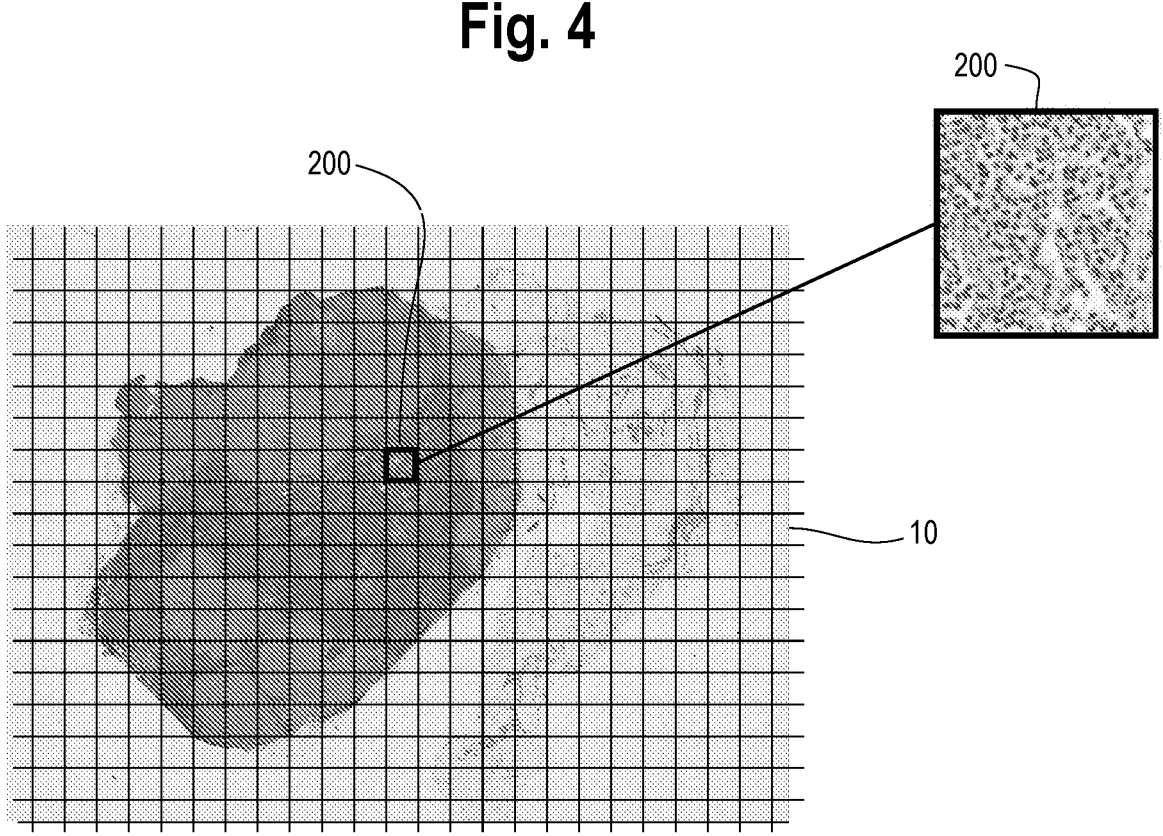
FIG. 4 is a detailed view of the slide image of FIG. 1A showing the division of the image into a multitude of patches, one of which is shown isolated to illustrate the cellular detail at 40×. The patches are not shown to scale in FIG. 4.

Still referring to FIG. 3, in the component 112 a final or ensemble score for the 128×128 pixel patch at 40× is generated from the outputs of each member of the ensemble, such as an average of the scores generated by each member (306A, 306B, 306O, 306D) of the ensemble. Each final or ensemble score is associated a different color (per the key or code of FIG. 2) and the patches are combined to generate a heatmap 20 (see also FIG. 1C). A score >0.9 means that the scoring algorithm has determined that the patch has the highest likelihood to have cancer cells. A score of 0.1-0.9 means that the algorithm does not have high enough confidence about the presence of metastasis. This often occurs with isolated tumor cells. A score ≤0.1 means that the algorithm has determined the patch is likely to be normal. In the heatmap the code or key of FIG. 2 is used to convert the scores to color in the heatmap representation. Of course, other grading scales or interpretations of the scores could be possible in alternative embodiments.

The representation of the heatmap 20 preferably further includes a list of the top 10 regions of interest. This is a list of 10 areas that are the most "suspicious" for the pathologist to review. This list is ranked by the size of the region (as measured by the longest dimension of a region), which is also shown to the pathologist. Crosshairs are generated in the heatmap to approximate the center of each region of interest. The original digitized image (see FIG. 1A) is displayed side by side with the heatmap. The software prompts the user to go over all 10 regions of interest to assess for metastasis at multiple zoom levels. The user can also then use caliper tools to confirm the size of the regions.

To generate the list of regions of interest, a threshold of 0.9 is applied to the image to generate a mask of tiles that have score ≥0.9 and <0.9. The mask is dilated 37.5 microns in all directions such that positive tiles that are within 75 microns of each other are considered contiguous. The software then calculates the largest dimension (diameter) and marks the center of each contiguous region and generates a list of up to 10 regions in order of largest dimension.

If less than 10 regions are provided, a threshold of 0.5 is then applied to the image to generate another binary mask of patches that have score ≥0.5 and <0.5. The mask is again dilated 37.5 microns in all directions such that positive patches that are within 75 microns of each other are considered contiguous. The software then calculates the largest dimension (diameter) and marks the center of each contiguous region and generates additional regions of interest until the maximum 10 regions of interest is provided.

If less than 10 regions are provided, this process is then repeated again for scores ≥0.1. The number of regions (10) can of course vary and is not particularly required. We have showed that we had sensitivity of ~94% at 8 false positives on average per slide for tumor localization (whereas human ability is at 73% sensitivity with 100% specificity), so 10 is a reasonable number of regions of interest to present to the user.

The pathologist is then prompted to review the ranked list of regions of interest. The pathologist can also at any time toggle back to see the full heatmap. The slide is considered reviewed if the pathologist has looked the ranked list of regions of interest. After review, the pathologist will be prompted to enter in the final results for the slide.

Figure 5:
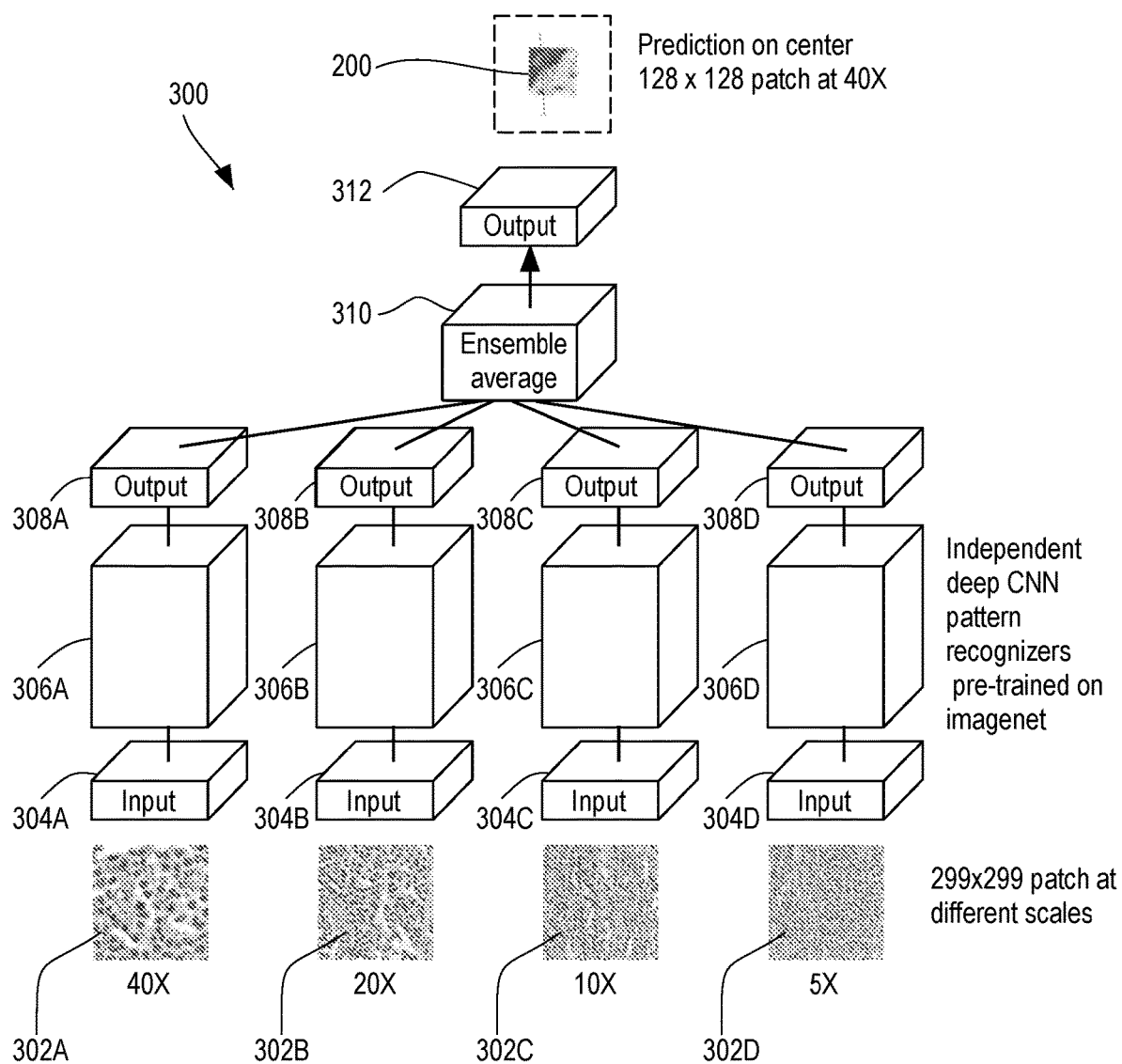
FIG. 5 is a block diagram of the ensemble of deep neural network pattern recognizers which are used to generate the score for each of the patches of FIG. 4. The ensemble of FIG. 5 can be considered a software system which may reside on a pathologist workstation or may alternatively reside on one or more computers in a local or wide area network.

Ensemble of Deep Neural Network Pattern Recognizers 306 (FIG. 5)

FIG. 5 is a block diagram of the ensemble 300 of deep convolutional neural network pattern recognizers 306A, 306B, 306C, 306D and a module 310 which combines the outputs from each pattern recognizer to generate a final or ensemble score for each of the patches of FIG. 4. The ensemble of FIG. 5 can be considered a software system which may reside on a pathologist workstation or may alternatively reside on one or more computers in a local or wide area network, in which case the workstation includes an application programming interface to the ensemble 300.

The ensemble was developed using a deep neural network approach. Specifically, a convolutional neural net model based on Google's Inception-v3 (also known as GoogleLeNet) was used and modified to classify abnormal tissue in image patches without explicit feature engineering. For the lymph node cancer cell embodiment, the development dataset consisted of 269 digitized slides from unique lymph node specimens, which consisted of 159 normal slides and 110 slides with the presence of tumor cells. Our sources of slide images for training included Naval Medical Center in San Diego, Calif. (NMCSD) and publicly available sources such as from the CAMELYON16 challenge and The Cancer Genome Atlas. Masks of tumor regions (see FIG. 1B) were generated using a combination of immunohistochemical (IHC) stains for cytokeratin and visual inspection of the H&E stain by pathologists. (It will be understood that a development set recognizing tumor cells in other types of tissues may make use of additional or different development sets, such as a set of say 300 digital slides of normal and cancerous prostate tissue obtained by biopsy, scanned and digitized at 40×).

Four different networks (306A, 306B, 306C, 306C) were trained corresponding to 5×, 10×, 20×, and 40× magnification. For each network, a single whole slide image was tiled into 299×299 pixel image patches, see 302A, 302B, 302C and 302D, one at 40×, one at 20×, one at 10× and one at 5×. Each member of the ensemble has its own input 304A, 304B, 304C, 304D, namely the pixel data for a 128×128 patch plus surrounding pixel data, at the respective magnification level, e.g., the 299×299 pixel square centered on the 128×128 patch as shown at 302. Each network 306A, 306B, 306C, 306D was then trained to predict whether the central 128 pixel square patch contained tumor cells based upon a larger 299 pixel square which shared the same center point as the 128 pixel square patch. This larger 299×299 pixel square is shown at 302 and at the top of FIG. 5 in dashed lines surrounding the 128×128 patch 200. Each network 306A, 306B, 306C, 306D generates its own output 308A, 308B, 308C, 308D in the form of a score between 0 and 1.

The score between 0 and 1 is usually generated as the last layer of the neural network pattern recognizers 306A. 306B, 306C, 306D, in the form of a multinomial logistic regression, which generates a prediction, in the form of a probability of between 0 and 1, of which of the classes (here, healthy vs tumor) the input data (patch) belongs to. Multinomial logistical regression is known in the art of supervised learning and optimization, and is sometimes referred to as "Softmax Regression."

The outputs 308A-308D of each of the pattern recognizers 306A-306D is then combined in module 310. In one embodiment, the prediction at each location is averaged across the ensemble to generate an average score between 0 and 1 for the likelihood that the 128 pixel by 128 pixel image patch at 40× was positive for the metastasis. As an ensemble output 312 the ensemble or average score for the patch is then converted to a color (or grayscale) per the code or key 22 (FIG. 2). This process proceeds for every patch 200 in the image (see FIG. 4) and the overall aggregate of patches represented as a heatmap, see FIG. 1C, and provided for display on a pathologist workstation.

The module "ensemble average" 310 in FIG. 5 could be implemented in a variety of ways. These include:
1. Code that computes the median score from the pattern recognizer outputs 308A-308D.
2. Code that computes a simple linear average over the pattern recognizer outputs 308A-308D.
3. Code that computes a weighted linear average over the prediction scores, where the relative weight for each pattern recognizer (a.k.a. "tower") is learned and represents the confidence into that particular pattern recognizers "vote" or score. For example, in some types of tissues, during training and development of the models it may discovered that a pattern recognizer operating on input patches at a particular magnification level. e.g., 5×, may perform at a higher accuracy (e.g., as determined by false positive or false negative rates) than other pattern recognizers at other magnifications. These performance metrics of the individual pattern recognizers can be learned and relative weights representing confidence in the score can be obtained and used to calculate a weighted linear average over the prediction scores.
4. Code implementing a convolutional neural network ("CNN"). If the training set is large enough we believe this approach may be the most effective and most generalizable one. In further detail, the input to this further convolutional neural network is a matrix for each pattern recognizer 306. Specifically, one option is to take the whole heatmap for each of the N pattern recognizers (a matrix consisting of an array of scores for each patch in the slide) and have the CNN use those N heatmaps as input to output one combined heatmap. A more general approach to this is that the input heatmaps are not only a 1-dimensional matrix of probabilities for each patch, but also a higher dimensional feature vector for each patch, e.g. the last layer of the CNN in the pattern recognizer before the logistic regression layer in each respective pattern recognizer 306. "Depth concatenation" is one way the stacking of N 1-d heatmaps into 1 N-d heatmap as input for a CNN.

Note that the model training in FIG. 5 makes use of pixel data surrounding the patch to generate the score. For example the patch 200 (e.g., 128×128 pixels) is analyzed in the context of surrounding tissue whereby the patch is located within, e.g., centered in a 299×299 region. Similarly, during the generation of patch scores of a given tissue image, while the ultimate prediction or score is assigned for that patch, the pattern recognizers use surrounding pixel data as explained above to determine a score for the 128×128 pixel patch. Obviously, at the extreme edges of the slide image the additional pixel data is only available on three sides of the patch and at the corner only at two of the edges of the patch. In any event, every given pixel patch is analyzed in a larger context of adjacent or surrounding pixels.

Deep convolutional neural network pattern recognizers, of the type used in 306A-306D of FIG. 5, are widely known in the art of pattern recognition and machine vision, and therefore a detailed description thereof is omitted for the sake of brevity. The Inception-v3 deep convolutional neural network architecture, upon which the present pattern recognizers are based, is described in the scientific literature. See the following references, the content of which is incorporated by reference herein: C. Szegedy et al., *Going Deeper with Convolutions* (September 2014); C. Szegedy et al., *Rethinking the Inception Architecture for Computer Vision* (December 2015); see also US patent application of C. Szegedy et al., "Processing Images Using Deep Neural Networks", Ser. No. 14/839,452 filed Aug. 28, 2015. A fourth generation, known as Inception-v4 is considered an alternative architecture for the pattern recognizers 306. See C. Szegedy et al., *Inception-v4, Inception-ResNet and the Impact of Residual Connections on Learning* (February 2016). See also US patent application of C. Vanhoucke, "Image Classification Neural Networks", Ser. No. 15/395,530 filed Dec. 30, 2016. The description of the convolutional neural networks in these papers and patent applications is incorporated by reference herein.

Additionally, the convolutional neural networks mentioned in the Background section of this document present alternatives tor the architecture of the pattern recognizers 306A-D of FIG. 5.

Techniques to Improve Robustness and Avoid Overfitting

During training of the pattern recognizers of FIG. 5, it is considered preferred to perform image augmentation techniques on the training slides in order to improve robustness of the scoring algorithm and avoid overfitting to training data. These augmentation techniques include performing at least one and preferably all of the following operations:

1) Geometrically perturbing the images locally by warping (simulating local tissue expansion and compression and other morphological variations);

2) Perturbing the image color statistics (e.g. Hue, Saturation, Intensity or Value). We use TensorFlow's image library (tensorflow.cimage.random_X) to perturb color: bright ness with a maximum delta of 64/255; saturation with a maximum delta of 0.25, hue with a maximum delta of 0.25 and contrast with a maximum delta of 0.75.

3) Normalizing the image color statistics, e.g. to make all images look as if they were scanned by one normalized scanner model (white balance, contrast, etc.). This is a relatively common technique (e.g. P. Leo et al., *Evaluating stability of histomorphometric features across scanner and staining variations: prostate cancer diagnosis from whole slide images*, J. Med Imaging 2016 October 3(4):047502; B. Bejnordi et al., *Stain Specific Standardization of Whole Slide Histopathological Images*, IEEE transactions on Medical Imaging, Vo. 35 no 2 p. 404-415 February 2016). However, in contrast to most existing techniques, we perform the normalization without the need to segment nuclei vs stroma—which is commonly done to separate the purple and pink parts of the color distribution.

Normalization of image color statistics is performed using the following approach: in step 1, we separate color and intensity information of the image by mapping from the raw RGB values to a Hue-Saturation-Density-Space. Such techniques are described in van Der Laak et al., *Hue-saturation-density (hsd) model for stain recognition in digital images from transmitted light microscopy*. Cytometry 39(4), 275-284 (2000)"). This creates a 2D color space. In step 2, we fit a single Gaussian to the color coordinates in that 2D color space for each tissue-containing patch, and then determine transformation from those color coordinates to those of a reference image to which the colors should be normalized to. Further details are described in paper: Piti'e, F., et al., *The linear Monge-Kantoovitch linear colour mapping for example-based colour transfer*, 4$^{th}$ European Conference on Visual Media Production (2007). In step 3, we map the colors from the 2D color space back to RGB values using the inverse transform from step 1 to create the color normalized image patch.

Alternatively, it may be possible to train a deep neural network to do this normalization if sufficient training data is available. The result of this normalization can be an image from a "virtual median" scanner, or from a particular scanner that we use as reference.

Furthermore, during model training we use patches uniformly across the slides, which reduces bias towards the largest tumors. The image perturbations we perform boost the effect size of the training data. The model learns to be insensitive to variations in brightness, contrast, hue, saturation and intensity. We also train using rotations and left/right, up and down flips of the slides and further introduce jitter into the patches. In particular, we rotate the input patches by four multiples of 90 degrees, and left-right flips and repeat the rotations. All eight orientations are valid because pathology slides do not have canonical orientations. The use of jitter may help prevent memorization of exact patches and also increases the diversity of the patches. We add jitter to the patch extraction process such that each patch has a small x/y offset of up to 8 pixels. The magnitude of the color perturbations and jitter are lightly tuned using our validation set.

It will be further understood that the training of the ensemble of neural network pattern recognizers 306 of FIG. 5 can be and optionally is performed across all of the possible rotations and flips of slides and all the possible types of perturbations of the training images, as well as the normalizations, or just some of them. Further, three or more different training runs on the same model may be performed to assess performance.

Performance

Figure 6:
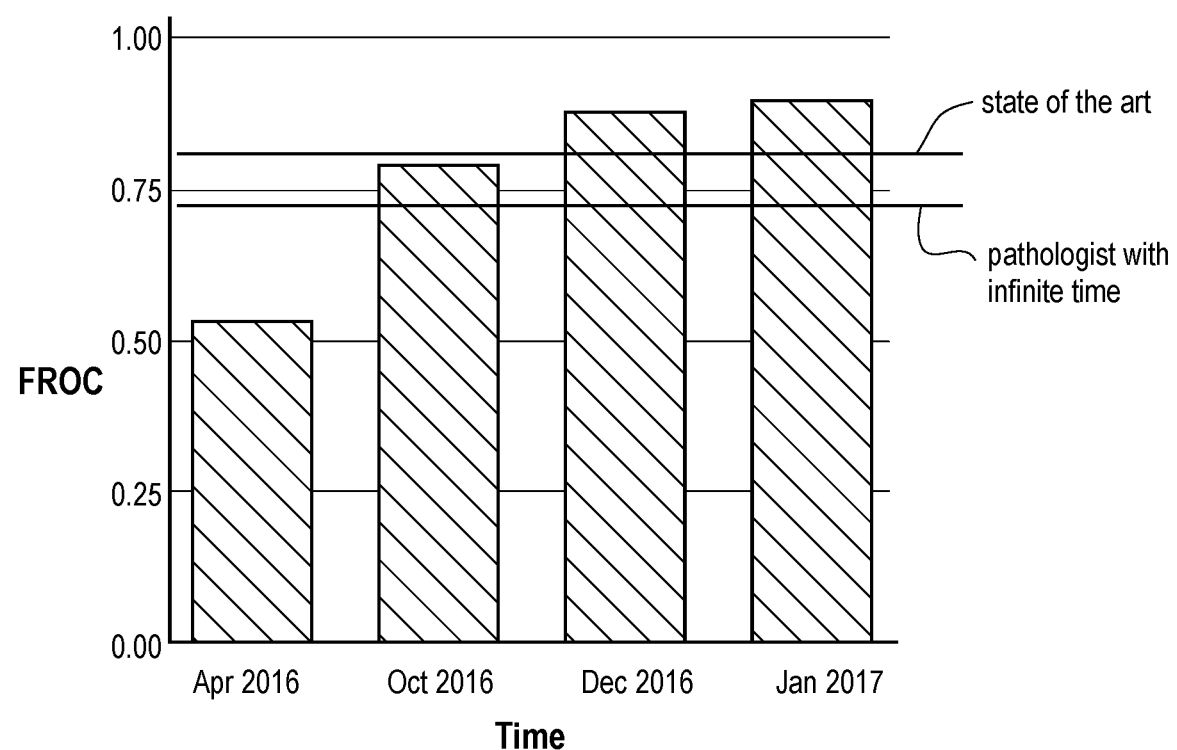
FIG. 6 is a plot of the tumor detection accuracy of the method we have developed shown in FIG. 3 over the period from April 2016 to January 2017.

FIG. 6 is a plot of the tumor detection accuracy of the method we have developed shown in FIG. 4 over the period from April 2016 to January 2017. In FIG. 6 the Y axis represents the free-response receiver operating characteristic (FROC) and is a measure of tumor detection accuracy in the present context. The accuracy has increased from our initial efforts in April 2016, at a level of approximately 0.53, steadily to our current performance of approximately 0.9, which is higher than the current state of the art or the ability of a trained pathologist with infinite time. The April 2016 results were using only one Inception-v3 pattern recognizer or trained model.

What we have termed as "per slide balancing" allowed us to achieve >75 percent accuracy by October 2016. We usually try to balance our training data such that there is roughly a similar number of training examples for all classes (in this case two classes, normal, tumor). If, for example, there are 10× fewer 'tumor' pixels in the whole data set than there are 'normal' pixels, we make sure to sample those tumor patches in training 10× more often than the normal so that, in total, they are balanced. We used to do this balancing over the whole set, i.e. we did not make sure that that 1:1 balanced between normal and tumor was true for each individual slide image, but only for the set as a whole. Changing that to make sure every slide itself is sampled in a balanced way is what is meant here by "per slide balancing." Additional improvements in performance resulted from additional model training replicas, and the implementation of the ensemble of deep learning pattern recognizers at four different magnifications.

Workstation and API

Figure 7:
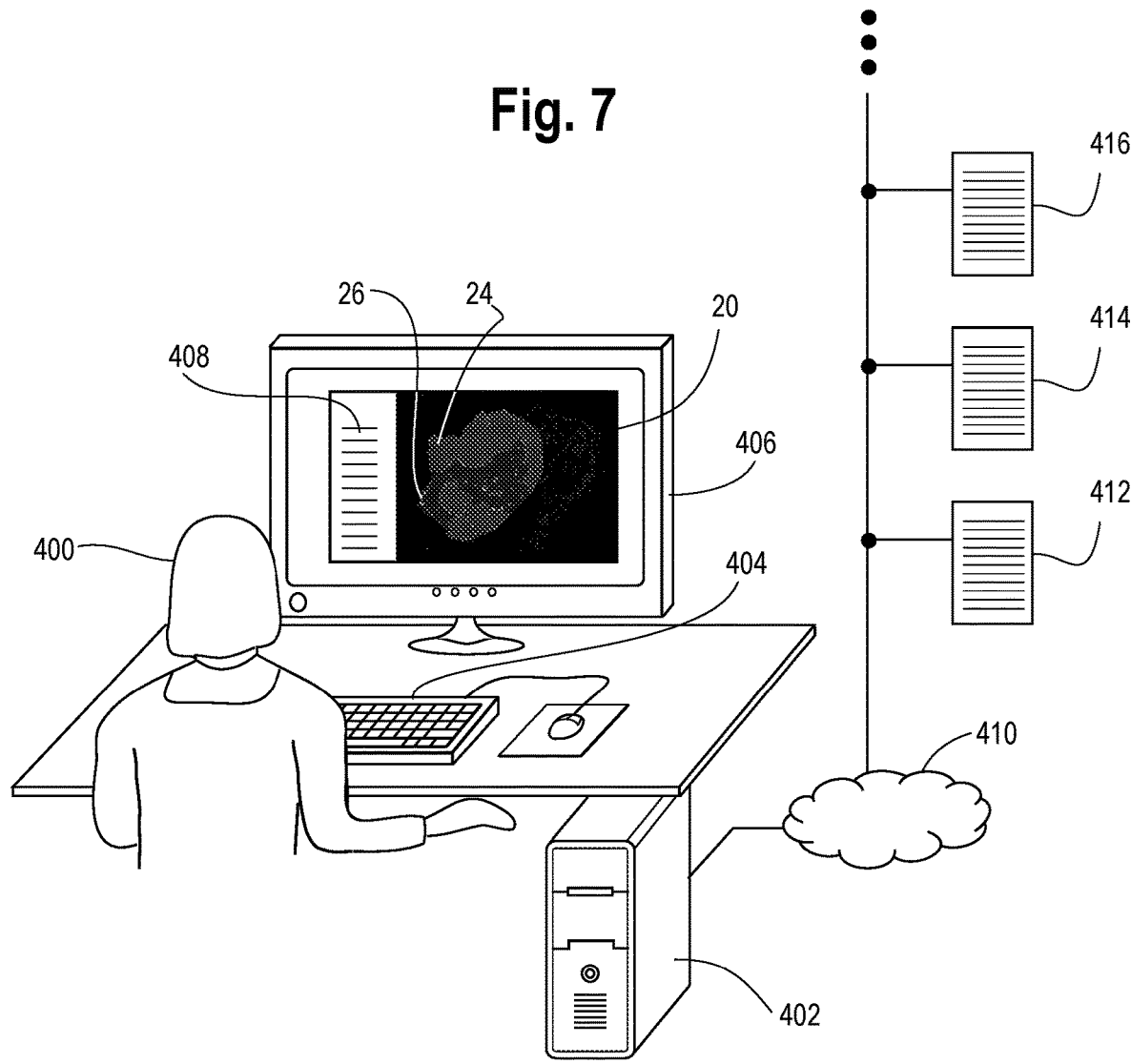
FIG. 7 is an illustration of a pathologist at a workstation using the heatmap of FIG. 1C to assist in identification of tumor cells in lymph node tissue.

FIG. 7 is an illustration of a pathologist 400 at a workstation 402 including keyboard 404 and display 406, using the heatmap 20 of FIG. 1C and a list of regions of interest 408 to assist in identification of tumor cells in lymph node tissue. The red areas 24 indicate areas of high probability of tumor cells and blue or violet areas 26 indicate areas of low probability of tumor cells. The workstation 402 may include a processor and software storing the ensemble of deep neural network pattern recognizers of FIG. 5. Alternatively, the workstation 402 could include software in the form of an application programming interface (API) which interfaces to the computer and software system 108 of FIG. 3, in which case the ensemble of deep neural network pattern recognizers of FIG. 5 could be implemented in remote computers 412, 412 and/or 416 which are connected to the workstation 402 via a local or wide area network 410. For computational efficiency reasons, it may be advantageous to deploy the ensemble of pattern recognizers over multiple computing platforms in order to reduce or eliminate latency in generating the heatmaps from an input whole slide digital image at 40× and allow the pathologist to work as efficiently as possible. For example, in a hospital setting, the images may be digitized and stored on a host network remote from the pathologist office. The pathologist workstation has work flow software that guides the pathologist in evaluating slides but the processing of the image data in module 112 to score the individual patches could take place in remote computers connected via the API and the network 410.

The implementation of the software functions of FIG. 3 can be implemented as an API, as a browser-based web service, or as a part of an imaging or display device which is paired to a mobile or hand-held device or computer. Furthermore, the term "workstation" is intended to refer broadly to include, among other things, a desk-top computer, a laptop computer, a tablet computer, a head-up display and other mobile computers including smart phones or special purpose handheld devices.

CONCLUSION AND FURTHER CONSIDERATIONS

From the forgoing description, in one aspect there is provided a method for analyzing a tissue biopsy. The method comprises (a) receiving image data representing tissue from the tissue biopsy, the image data obtained at a first magnification (e.g., 40×); (b) subdividing the image data into a plurality of patches (see FIG. 4), each patch comprising a portion of the image data representing a respective portion of the tissue from the tissue biopsy; and (c) for each of the patches, determining a likelihood of malignancy score, wherein the score is obtained by processing the patch using an ensemble of deep neural network pattern recognizers, and combining the outputs of each of the deep neural network pattern recognizers, wherein the ensemble of deep neural network pattern recognizers are arranged to process the patch at a plurality of levels of magnification including the first magnification (e.g. 40×) and a second magnification, e.g., 20×, 10× or 5×.

The method may further comprise assigning a value to each patch in accordance with the likelihood of malignancy score assigned to the patch by the deep neural network pattern recognizer. Output data representing the tissue, e.g., a heatmap as shown in FIG. 1C, from the tissue biopsy may be generated based upon the assigned values.

The method may further comprise training the ensemble of pattern recognizers using a plurality of training images. At least one training image of the plurality of training images may be generated by performing at least one operation on at least one image representing tissue from a tissue biopsy. The at least one operation may comprise a modification of image data represented in the at least one image representing tissue from the tissue biopsy. The at least one operation may be selected from the group consisting of: 1) performing geometric perturbations to the training images, 2) performing image color statistics perturbation on the training images, 3) normalization of image color statistics of the training images, 4) rotations, up/down and left/right flips of the training images, and 5) introduction of jitter into the training images. The method may comprise performing one or more combinations of the operations to generate the at least one training image. For example, a plurality of images representing tissue may be obtained. The ensemble of pattern recognizers may be trained using the plurality of images representing tissue and further training images generated based upon the plurality of images.

The method may further comprise using both image data in the patch and image data from a region of the image surrounding each patch to assign the likelihood of malignancy score to the patch. The region of the image data surround the patch may comprise image data representing a portion of the tissue from the tissue biopsy adjacent to the portion of the tissue represented by the patch, or for example image data representing a portion of the tissue surrounding the patch.

The patch may comprise a square or rectangular region comprising a plurality of pixels. The region may be centered within the portion of the image data representing the respective portion of the tissue from the tissue biopsy represented by the patch.

Processing each patch at a plurality of levels of magnification may comprise processing a first portion of the image data representing the portion of the tissue from the tissue biopsy associated with the patch; and processing a second portion of the image data comprising the first portion of the image data and additional image data representing a portion of the tissue from the tissue biopsy surrounding the portion of the tissue from the tissue biopsy associated with the patch. Each of the plurality of levels of magnification may represent a different portion of the tissue from the tissue biopsy including the portion of the tissue biopsy associated with the patch. Each of the plurality of levels of magnification may, for example, comprise an array of pixels such as a two-dimensional array of pixels, each of the arrays of pixels representing a portion of the image data comprising the first portion of the image data. Each of the arrays of pixels may be of the same size. That is, each array of pixels may comprise a corresponding number of pixels. Pixels in arrays associated with different levels of magnification may therefore represent different portions of the tissue from the tissue biopsy of different sizes.

The method may further comprise initially performing an image quality assessment for each patch. The method may comprise determining a score for the patch if the image quality assessment determines that the patch is gradable. That is, the score may indicate whether the image data representing the patch is of sufficiently high quality for further processing. The image quality assessment for the patch may be performed by a trained neural network. The method may further comprise generating a list of regions of interest present in the representation.

It will be further appreciated that we have described a method for assisting a pathologist (pathologist 400 in FIG. 7) in identifying tumor cells (24, FIG. 1C) in tissue obtained from a biopsy, e.g., lymph node or prostate tissue, comprising the steps of:

(a) Obtaining a digital image (FIG. 1A) at a first magnification, e.g., 40×, of a slide containing the tissue.

(b) Subdividing the digital image into a multitude of patches (see FIG. 4), each patch comprising a portion of the digital image representing a respective portion of the tissue. The patch may be any two dimensional array of pixels, such as a rectangular or square array.

(c) For each of the patches 200, determining a likelihood of malignancy score, wherein the score is obtained by analyzing pixel data in the digital image including the patch using an ensemble of deep neural network pattern recognizers (FIG. 5, 306) at multiple levels of magnification including the first magnification (e.g., 40×) and at least a second magnification (e.g., 20×) centered on or containing the patch, and combining the outputs of each of the deep neural network pattern recognizers. And, (d) Generating a representation of the slide (FIG. 1C, FIG. 7, heatmap 20) for the pathologist wherein each of the patches is assigned a color in accordance with (1) the likelihood of malignancy score assigned to the patch by the deep neural network pattern recognizer and (2) a code (22, FIG. 2) assigning distinct colors or grey scale values to different values of likelihood of malignancy scores assigned to the multitude of patches.

In preferred embodiments image augmentation is performed during training of the ensemble of models, including performing at least one of the following operations: geometric perturbations, image color statistics perturbation, normalization of image color statistics, rotations and up/down flips of training images, and introduction of jitter.

In preferred embodiments the models are trained using image data surrounding the patch to generate scores by each member of ensemble.

Optionally an initial image quality assessment is performed for each patch. A trained neural network can be used to make this image quality assessment.

The heatmap is preferably generated along with a list of regions of interest, which may be ranked or ordered by size. Crosshairs can be generated in the heatmap to approximate the center of each region. The original digitized image may be displayed side by side with the heatmap. The software will then prompt the user to go over all regions of interest to assess for metastasis at multiple zoom levels. The user can also then use caliper tools to confirm the size of the regions.

In another aspect, it will be appreciated that we have disclosed a computer system (e.g., FIG. 7 workstation 400, or remote computer 412) which is programmed as a machine for assessing the likelihood of presence of tumor cells in digital slide containing lymph node tissue. The computer includes an ensemble of deep neural network pattern recognizers (FIG. 5, 306), each trained on a multitude of digital slide images of lymph node tissue at a particular and different magnification level of the digital slide images (e.g., 40×, 20×, 10× and 5×). Each member of the ensemble generates an output (FIG. 5, 308) in the form of a likelihood of malignancy score for a patch 200 of the digital slide 10 containing lymph node tissue. The outputs of each of the members of the ensemble are combined (FIG. 5, 310) to generate an overall or ensemble likelihood of malignancy score for the patch.

While the ensemble of neural networks of FIG. 5 are shown as having separate inputs, it is possible that a single input could be provided (e.g., 40× pixel data for patch being analyzed) to the ensemble and the pattern recognizer for other magnifications performs an initial step of downsampling to obtain the pixel data for the magnification for which the model was trained. Obviously there can be these and other variations in the design of the architecture of FIG. 5 without departure from the scope of the invention.

In still another aspect, a system (FIG. 3, 7) is disclosed for assisting a user (e.g., pathologist) in identifying tumor cells in a tissue sample obtained from a biopsy. The system includes a workstation 400 (FIG. 7) configured to display a magnified digital image of a slide containing the tissue. The system further includes an application programming interlace (API) to a software system (FIG. 3) configured as an ensemble of deep neural network pattern recognizers (FIG. 5), each trained on a training set comprising multitude of digital slide images of benign and cancerous tissue at a particular and different magnification level of the digital slide images. The software system (FIG. 3) is further configured to subdivide the digital image into a multitude of patches (FIG. 4), each patch in the form of a rectangular array of pixels. The software system is further configured for determining, for each of the patches, a likelihood of malignancy score, wherein the score is obtained by analyzing pixel data in the digital image including the patch using the ensemble of deep neural network pattern recognizers (FIG. 5, 306). The workstation 400 is further configured to present on the display a representation of the slide (i.e., heatmap 20) wherein each of the patches is assigned a color or equivalent (e.g. grayscale value) in accordance with (1) the likelihood of malignancy score assigned to the patch by the ensemble of deep neural network pattern recognizers and (2) a code, e.g., key or other assignment mechanism (see 22, FIG. 2) which assigns distinct colors (or equivalently grayscale values) to different values of likelihood of malignancy scores assigned to the patches.

Aspects can be implemented in any convenient way. For example, other example aspects of the present disclosure are directed to systems, apparatus, tangible, non-transitory computer-readable media, user interfaces, memory devices, and electronic devices for analyzing a tissue biopsy.

The appended claims are offered as further descriptions of the disclosed invention.

We claim:

1. A method for analyzing a tissue biopsy, the method comprising:
   (a) obtaining first image data representing tissue from the tissue biopsy, the first image data obtained at a first magnification;
   (b) obtaining second image data, the second image data representing tissue from the tissue biopsy, the second image data associated with a second magnification, the second image data obtained at the second magnification or from a downsampling or upsampling of the first image data obtained at the first magnification;
   (c) subdividing the first image data into a plurality of first patches, wherein each first patch is a two-dimensional array of pixels, each first patch comprising a portion of the first image data representing a respective portion of the tissue from the tissue biopsy, wherein each first patch comprises an inner patch and a region surrounding the inner patch, wherein the second image data comprises a plurality of second patches, wherein each second patch is a two-dimensional array of pixels, wherein each second patch comprises an inner patch and a region surrounding the inner patch, and wherein each first patch is centered on or contains a corresponding second patch; and
   (d) for each of the first patches, determining a likelihood of malignancy score for the inner patch of the first patch, wherein the score is obtained by processing the first patch and the corresponding second patch using an ensemble of deep neural network pattern recognizers and combining outputs of each of the deep neural network pattern recognizers, wherein a first deep neural network pattern recognizer of the ensemble of deep neural network pattern recognizers is arranged to process the first patch at the first magnification and to analyze the inner patch of the first patch in a context of the region surrounding the inner patch of the first patch, and wherein a second deep neural network pattern recognizer of the ensemble of deep neural network pattern recognizers is arranged to process the corresponding second patch at the second magnification and to analyze the inner patch of the corresponding second patch in a context of the region surrounding the inner patch of the corresponding second patch.

2. The method of claim 1, further comprising:
   assigning a value to each first patch in accordance with the likelihood of malignancy score determined for the inner patch of the first patch; and
   generating output data representing the tissue from the tissue biopsy based upon the assigned values.

3. The method of claim 1, further comprising the step of training the ensemble of pattern recognizers using a plurality of training images, wherein at least one training image of the plurality of training images is generated by performing at least one operation on the training image, the at least one operation selected from the group consisting of:
   1) performing geometric perturbations to the training image;
   2) performing image color statistics perturbation on the training image, wherein the image color statistics comprise hue, saturation, intensity, value, or contrast;
   3) normalization of image color statistics of the training image;
   4) rotations, up/down and left/right flips of the training image; and
   5) introduction of jitter into the training image, such that each patch of the training image has an x/y offset of up to 8 pixels.

4. The method of claim 1, further comprising the step of training the ensemble of pattern recognizers using a plurality of training images, wherein at least one training image of the plurality of training images is generated by:
   1) performing geometric perturbations to the training image;
   2) performing image color statistics perturbation on the training image, wherein the image color statistics comprise hue, saturation, intensity, value, or contrast;
   3) normalization of image color statistics of the training image;
   4) rotations, up/down and left/right flips of the training image; and 5) introduction of jitter into the training image, such that each patch of the training image has an x/y offset of up to 8 pixels.

5. The method of claim 1, wherein the first patch comprises a square region of pixels, and wherein the square region of pixels is centered within the region of the first image data surrounding the first patch.

6. The method of claim 1, wherein the corresponding second patch comprises a square region of pixels, and wherein the square region of pixels is centered within the region of the second image data surrounding the corresponding second patch.

7. The method of claim 1, further comprising generating a list of regions of interest present in the first image data representing tissue from the tissue biopsy, wherein the likelihood of malignancy score is between 0 and 1, wherein the regions of interest are areas for a pathologic to review, and wherein the list is generated by:
 applying a threshold of 0.9 to the output data to generate a mask of patches that have a likelihood of malignancy score equal to or greater than 0.9, wherein if patches from the mask of patches are within 75 microns of each other the patches are considered to form a continuous region;
 determining a largest dimension of each continuous region; and
 ordering the continuous regions based on the largest dimension to generate the list, wherein the list comprises a maximum of 10 regions of interest.

8. The method of claim 1, further comprising initially performing an image quality assessment for each patch and proceeding to determine a score for the patch if the image quality assessment determines that the patch is gradable.

9. The method of claim 8, wherein the image quality assessment for the patch is performed by a trained neural network, wherein the neural network is trained using labeled training patches, each patch comprising a portion of training image data representing tissue from tissue biopsies, and wherein the patches have been labeled gradable or not gradable.

10. The method of claim 1, further comprising generating a list of regions of interest present in the first image data representing tissue from the tissue biopsy.

11. A non-transitory computer-readable medium carrying a computer program comprising computer-readable instructions arranged to cause a computer to carry out a method according to claim 1.

12. A computer apparatus for analyzing a tissue biopsy comprising:
 a memory storing processor-readable instructions; and
 a processor arranged to read and execute the processor-readable instructions,
 wherein the processor-readable instructions comprise instructions arranged to control the computer to carry out the method of claim 1.

13. A computer system programmed as a machine for assisting a pathologist in assessing a likelihood of presence of tumor cells in a digital slide containing tissue from a tissue biopsy, comprising:
 an ensemble of deep neural network pattern recognizers, wherein the ensemble of deep neural network pattern recognizers comprises a first deep neural network pattern recognizer and a second deep neural network pattern recognizer, wherein the first deep neural network pattern recognizer is trained on a multitude of digital slide images of tissue at a first magnification, wherein the second deep neural network pattern recognizer is trained on the multitude of digital slide images of tissue at a second magnification,
 wherein the first deep neural network pattern recognizer is arranged to process a first patch of subdivided first image data at the first magnification and to analyze an inner patch of the first patch in a context of a region surrounding the inner patch of the first patch, wherein the first patch comprises a portion of the first image data representing the tissue from the tissue biopsy at the first magnification, wherein the first patch is a two-dimensional array of pixels, wherein the first patch is centered on or contains a corresponding second patch of subdivided second image data at a second magnification,
 wherein the second deep neural network pattern recognizer is arranged to process the corresponding second patch at the second magnification and to analyze an inner patch of the corresponding second patch in a context of a region surrounding the inner patch of the second corresponding patch, wherein the second image data represents the tissue from the tissue biopsy at the second magnification, wherein the second image data was obtained at the second magnification or from a downsampling or upsampling of the first image data obtained at the first magnification, and wherein the corresponding second patch is a two-dimensional array of pixels; and
 code that combines the outputs of the first deep neural network pattern recognizer and the second deep neural network pattern recognizer to determine a likelihood of malignancy score for the inner patch of the first patch.

14. The computer system of claim 13, wherein the code that combines the outputs of the first deep neural network pattern recognizer and the second deep neural network pattern recognizer: (a) computes a median score from the outputs; (b) computes a linear average over the outputs; or (c) computes a weighted linear average.

15. The computer system of claim 13, wherein the code that combines the outputs of the first deep neural network pattern recognizer and the second deep neural network pattern recognizer implements a convolutional neural network.

16. The computer system of claim 13, wherein the computer system is implemented on a pathologist workstation.

17. The computer system of claim 13, wherein the computer system is implemented on one or more computers remote from a pathologist workstation.

18. The computer system of claim 13, further comprising a trained neural network performing image quality assessment for the first patch.

19. The computer system of claim 15, wherein each member of the ensemble of deep neural network pattern recognizers is trained using a multitude of training images containing tumor patches and normal patches, and wherein for each of the training images the tumor patches are sampled more often than the normal patches during training of the members of the ensemble of deep neural network pattern recognizers.

20. A system for assisting a pathologist in identifying tumor cells in a tissue obtained from a tissue biopsy, comprising:
 a workstation configured to display a magnified digital image of a slide containing tissue obtained from the tissue biopsy; and
 an application programming interface (API) to a software system configured as an ensemble of deep neural network pattern recognizers, wherein the ensemble of deep neural network pattern recognizers comprises a first deep neural network pattern recognizer and a second deep neural network pattern recognizer, wherein the first deep neural network pattern recognizer is trained on a multitude of digital slide images of tissue at a first magnification, wherein the second deep neural network pattern recognizer is trained on the multitude of digital slide images of tissue at a second magnification, wherein the first deep neural network pattern recognizer is arranged to process a first patch of subdivided first image data at the first magnification and to analyze an inner patch of the first patch in a context of a region surrounding the inner patch of the first patch, wherein the first patch comprises a portion of the first image data representing the tissue from the tissue biopsy at the first magnification, wherein the first patch is a two-dimensional array of pixels, wherein the first patch is centered on or contains a corresponding second patch of subdivided second image data at a second magnification, wherein the second deep neural network pattern recognizer is arranged to process the corresponding second patch at the second magnification and to analyze an inner patch of the corresponding second patch in a context of a region surrounding the inner patch of the second corresponding patch, wherein the second image data represents the tissue from the tissue biopsy at the second magnification, wherein the second image data was obtained at the second magnification or from a downsampling or upsampling of the first image data obtained at the first magnification, and wherein the corresponding second patch is a two-dimensional array of pixels, wherein the software system is further configured to determine, for each inner patch of the patches in the first image data, a likelihood of malignancy score, wherein the score is obtained by combining outputs of the first deep neural network pattern recognizer and the second deep neural network pattern recognizer, and wherein the software system is further configured to present on the workstation a representation of the slide wherein each of the inner patches in the first image data is assigned a color or grayscale in accordance with (1) the likelihood of malignancy score assigned to the inner patch and (2) a code assigning distinct colors or grayscale values to different values of likelihood of malignancy scores assigned to the inner patches.

\* \* \* \* \*